US012465496B2

(12) United States Patent
Alden

(10) Patent No.: US 12,465,496 B2
(45) Date of Patent: Nov. 11, 2025

(54) PROSTHETIC COMPONENET EXTRACTOR

(71) Applicant: Kris Alden, Austin, TX (US)

(72) Inventor: Kris Alden, Austin, TX (US)

( * ) Notice: Subject to any disclaimer, the term of this patent is extended or adjusted under 35 U.S.C. 154(b) by 1172 days.

(21) Appl. No.: 17/359,950

(22) Filed: Jun. 28, 2021

(65) Prior Publication Data

US 2021/0330476 A1 Oct. 28, 2021

Related U.S. Application Data

(63) Continuation-in-part of application No. 16/977,427, filed as application No. PCT/US2019/020437 on Mar. 1, 2019, now Pat. No. 11,382,766.

(60) Provisional application No. 62/637,075, filed on Mar. 1, 2018.

(51) Int. Cl.
*A61F 2/46* (2006.01)
*A61B 17/92* (2006.01)

(52) U.S. Cl.
CPC .......... *A61F 2/4607* (2013.01); *A61B 17/921* (2013.01); *A61F 2002/4619* (2013.01); *A61F 2002/4628* (2013.01)

(58) Field of Classification Search
CPC . A61B 17/92; A61B 17/921; A61B 2017/922; A61F 2/4607; A61F 2002/4619
See application file for complete search history.

(56) References Cited

U.S. PATENT DOCUMENTS

| | | | | |
|---|---|---|---|---|
| 5,443,471 A * | 8/1995 | Swajger | A61B 17/1659 | 403/324 |
| 8,142,439 B2 * | 3/2012 | Parker | A61F 2/34 | 606/86 R |
| 8,157,808 B2 * | 4/2012 | Keller | A61F 2/4607 | 606/89 |
| 9,603,719 B2 * | 3/2017 | Andrews | A61F 2/461 | |
| 11,399,961 B2 * | 8/2022 | Gosik-Wolfe | A61F 2/4603 | |
| 11,612,501 B2 * | 3/2023 | Pendleton | A61F 2/461 | 606/84 |
| 11,622,869 B2 * | 4/2023 | Alden | A61B 17/921 | 606/99 |
| 11,723,781 B2 * | 8/2023 | Sweitzer | A61F 2/4603 | 606/99 |
| 2008/0033444 A1 * | 2/2008 | Bastian | A61B 17/1668 | 606/85 |
| 2010/0121331 A1 * | 5/2010 | Sharp | A61B 17/1668 | 606/80 |
| 2015/0245920 A1 * | 9/2015 | Andrews | A61F 2/461 | 606/99 |
| 2016/0206443 A1 * | 7/2016 | Brooks | A61F 2/4607 | |
| 2019/0336307 A1 * | 11/2019 | Sungu | A61F 2/3662 | |
| 2019/0374349 A1 * | 12/2019 | Müller | A61F 2/4607 | |

FOREIGN PATENT DOCUMENTS

| | | | |
|---|---|---|---|
| EP | 0550118 B1 * | 12/1992 | A61F 2/4607 |

* cited by examiner

*Primary Examiner* — Anu Ramana

(57) ABSTRACT

The present device described herein is intended to effect the removal of an orthopedic prosthetic implant from the intramedullary cavity of the bone. The extraction device utilizes a clamping mechanism which can be tightly secured to the implant, particularly the neck of a femoral prosthetic component. The clamping mechanism is attached to an elongated member that contains two striking surfaces. A force applied to the striking surface(s) is transmitted to the prosthesis so as to extract the implant from the intramedullary cavity of a bone.

15 Claims, 15 Drawing Sheets

Fig. 4A
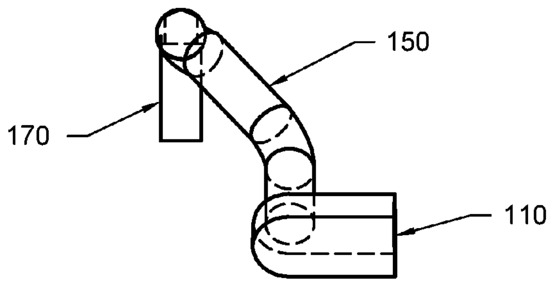
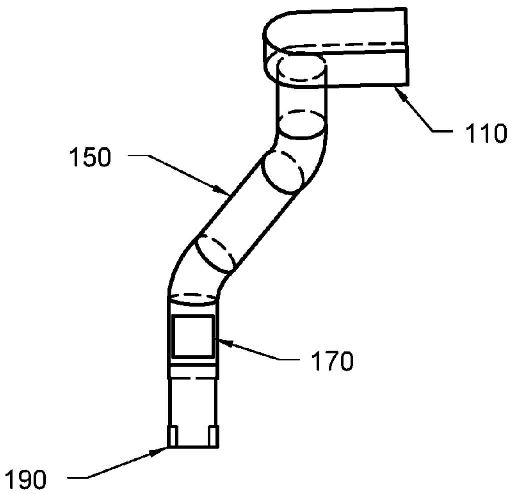
Fig. 4B
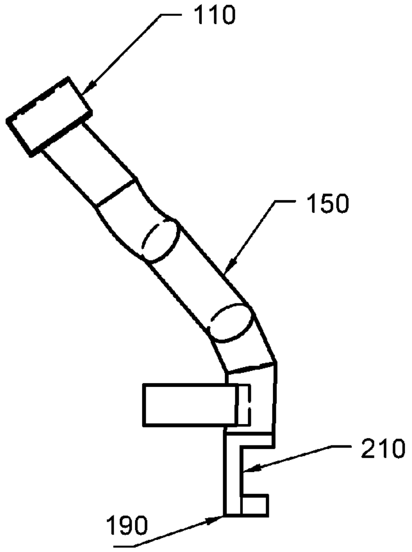
Fig. 4C

Fig. 5B
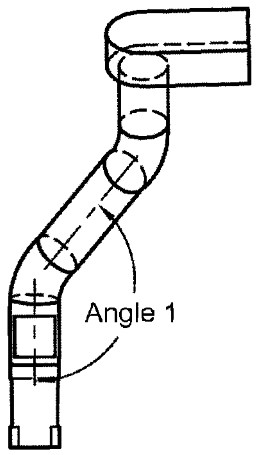
Fig. 5C
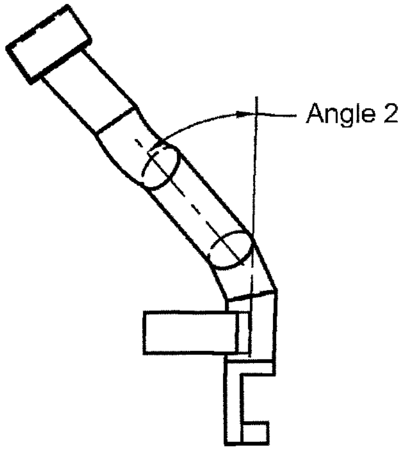
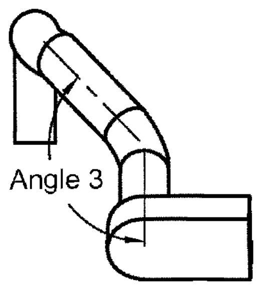
Fig. 5A
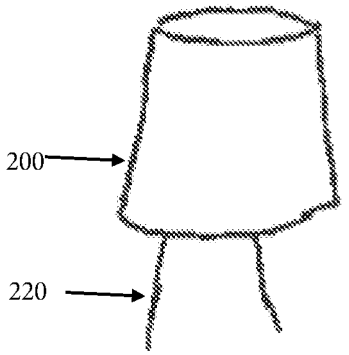
Fig. 6

PROSTHETIC COMPONENET EXTRACTOR

CROSS-REFERENCE TO RELATED APPLICATIONS

This application is a continuation-in-part of U.S. patent application Ser. No. 16/977,427, filed Sep. 1, 2020, which is a § 371 national phase entry of International Application No. PCT/US2019/020437, filed Mar. 1, 2019, which claims priority to U.S. Provisional Patent Application No. 62/637,075, filed Mar. 1, 2018, the entirety of which is incorporated herein by reference.

FIELD OF THE INVENTION

The present disclosure relates to devices for extracting artificial joints, implants, or orthopedic prosthetics from the intramedullary cavity of a bone.

SUMMARY OF THE RELATED ART

Unless otherwise indicated herein, the materials described in this section are not admitted to be prior art to the claims in this application.

Load-carrying joints, such as the hip, can be rendered painful and thereby nonfunctional due to a multitude of disease states such as arthritis, fracture, or congenital deformity. The end result of the various pathophysiologic processes that impact a joint include degeneration, resulting in pain and loss of function for the individual. Joint replacement procedures with prosthetic implants have successfully treated and resolved numerous conditions that result in degeneration of the affected joints. Due to both an aging population and younger patients desiring a more active lifestyle not impaired by degenerative conditions, joint replacement surgeries are becoming increasingly common.

In traditional procedures, implants can be affixed to the bone in one of two ways: (i) through cementing the implant into place, or (ii) through biologic fixation after impacting the implant into the medullary cavity of the bone. The un-cemented implants achieve bone ingrowth and boney integration onto the surface of the implant thereby obtaining biologic fixation. Knee, hip, and shoulder replacement procedures are the most commonly performed joint replacements worldwide. Hip implants, in particular, include an acetabular component, which is affixed to the pelvis, and a femoral component, which is secured to the proximal femur. The femoral component accepts a head component, which is fixed through a morse taper that articulates in a liner of the acetabular component. The liner is secured into the acetabular component which is affixed to the pelvis most commonly through cementless fixation.

The widespread adoption of orthopaedic implants to ameliorate degenerative joint conditions also has an important corollary: a variable percentage of prosthetic implants will ultimately fail. These prosthetic failures are due to a variety of etiologies including implant loosening, infection, dislocation, instability, and periprosthetic fracture. The failed implants must be removed during revision joint replacement procedures, whereby revision prosthetics are implanted to allow for pain relief, mobility, and enhance the function of the individual. The current methodologies and tools available for the removal of prosthetics are generally rudimentary and have not evolved to facilitate modern and less invasive surgical techniques. The presently available implant removal tools require longer operative times, enlarged surgical dissection and incisions, and have overall less favorable success rates than primary joint replacement procedures.

The bond that retains the component in the bone (either cement or biologic fixation) must be broken to facilitate removal of the failed implant and to permit the implantation of the revision components. Should the current tools fail to achieve removal of the implant, surgical techniques to affect prosthetic removal include cutting the bone, i.e., performing an osteotomy. The revision joint replacement procedures that require an osteotomy are more invasive, painful, of longer duration, further require osteotomy healing, and significantly prolong the recovery time for the patient. The physical work to remove well-fixed implants during a revision type surgical procedure can result in muscle, tissue, and bone damage, produce physical stress on the surgeon, and thereby require longer operative times, reduce native host bone stock, increase the risk of postoperative surgical complications, and require longer patient recovery periods.

Commonly used surgical disimpaction techniques typically begin with the use of osteotomes to initially break the proximal bond between the implant and the host bone. This part of the surgical procedure and the associated instrumentation are generally limited in both the scope and depth of penetration in and around the component. Once the maximal safe depth of penetration into the host bone is attained, further extraction techniques are required. Retrograde disimpaction of a femoral component through the employment of bone tamps can be used, but such a procedure is predicated on the implant having a collar or reasonable striking surface to impact and thereby dislodge the component. In addition, retrograde disimpaction may also require excessive bone removal and is generally ineffective due to the significant loss of force operating through an inferior vector through which the surgeon must direct the appropriate force. Antegrade removal of a prosthetic implant is thereby the generally preferred surgical technique, as the surgeon has easier access to the orthopaedic implant. Several modern prosthetic implants have a screw hole in the shoulder of the implant that can be used to affix an extraction device. However, these screw holes are generally inaccessible during the extraction phase of the revision joint replacement procedure and, therefore, are rarely helpful to effect extraction.

Attaching an extraction instrument to the trunnion of the femoral implant is a more facile approach to effect surgical implant removal. Such methods generally employ fixing an extractor to the proximal part of the prosthetic implant with pliers (or a similar instrument) and striking the instrument. Additionally, using a slaphammer device affixed to the implant to backslap the implant out of the bone can also be utilized. These devices are bulky, difficult to use, require greater surgical dissection, and generally do not permit the operator to generate sufficient force to break the bond between the implant and the host bone and thereby extract the implant.

SUMMARY

In view of the foregoing, it may be recognized that the above devices and methods are generally and practically ineffective in transmitting sufficient force to break the remaining bond between the implant and bone to thereby extract the prosthesis. Naturally, the force required to remove the implant must be less than the force that fixes the extractor to the implant, i.e. the fixation strength of the extractor to the implant must be greater than the force require to remove it. In the common scenario where the force required to remove the implant is greater than that achieved by the extractor, the extractor will ultimately fail to transmit sufficient force to the implant to effect its removal from the host bone. Therefore, a more facile, less invasive mechanism to exert force on the implant and thereby effect prosthetic implant removal may be desired.

Thus, in one embodiment, a device is provided. The device includes an elongated member having a first end and a second end, the elongated member comprising substantially straight, rod-like first, second, and third segments each having first and second ends, the first and second segments being connected by a first curved segment at their second and first ends, respectively, and the second and third segments being connected by a second curved segment at their second and first ends, respectively, and the first ends of each of the segments are proximal to the first end of the elongated member relative to the second ends of the segments. The device also includes a first striking surface positioned on the first segment extending away from the elongated member. The device also includes a second striking surface positioned on the third segment extending away from the elongated member. The device also includes a hook or clamp mechanism positioned at the second end of the third segment, wherein the hook includes a channel substantially perpendicular to a long axis of the third segment that is configured to engage a surgical implant.

In another embodiment of the invention, an orthopaedic femoral implant extractor device is described for use in the removal of implants from an intramedullary bone cavity. The device includes three (3) major sections. The three sections each make up essential components of the device. The first section contains a clamp mechanism that attaches to the orthopaedic implant. This first section is a substantially straight, rod-like segment which connects to the second section. The clamping mechanism includes a channel substantially perpendicular to the long axis that is configured to engage the orthopaedic implant. The second section is a curved segment and contains a first of two striking plates which is positioned to extend away from the elongated member. The third section is a substantially straight, rod-like segment that contains the second of two striking plates that extend away from the elongated member.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIGS. 4A-4C illustrates the front view, the right side view, and the top view of the example device of FIG. 1, respectively, according to an example embodiment.

FIGS. 5A-5C illustrate the front view, the right side view, and the top view of the example device of FIG. 1, respectively, including angles between the various components, according to an example embodiment.

FIG. 6 illustrates an example implant for extraction using the device of FIG. 1, according to an example embodiment.

DETAILED DESCRIPTION

Figure 1:
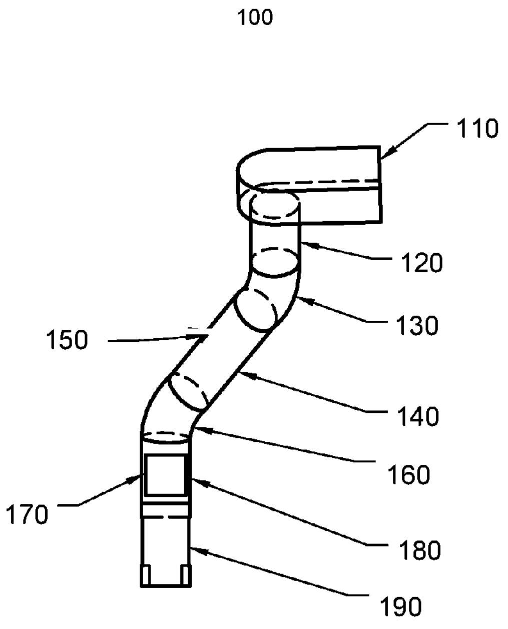
FIG. 1 illustrates a front view of an example device for a left hip, according to an example embodiment.
Figure 2:
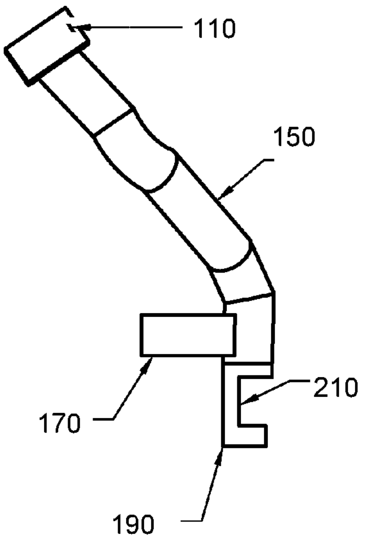
FIG. 2 illustrates a right side view of the example device for a left hip of FIG. 1, according to an example embodiment.

Exemplary devices and systems are described herein. It should be understood that the word “exemplary” is used herein to mean “serving as an example, instance, or illustration.” Any embodiment or feature described herein as “exemplary” is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" and "substantially" each means+/−5%.

As used herein, "coupled" means associated directly as well as indirectly. For example, a member A may be directly associated with a member B, or may be indirectly associated therewith, e.g., via another member C.

In the following description, numerous specific details are set forth to provide a thorough understanding of the disclosed concepts, which may be practiced without some or all of these particulars. In other instances, details of known devices and/or processes have been omitted to avoid unnecessarily complicating and obscuring the disclosure. While some concepts will be described in conjunction with specific examples, it will be understood that these examples are not intended to be limiting.

Unless otherwise indicated, the terms "first," "second," etc. are used herein merely as labels and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The present disclosure describes a prosthetic implant extraction device 100 to facilitate the surgical removal of a femoral component 270 of hip joint implant or intramedullary orthopaedic implant (cemented or uncemented intramedullary orthopaedic implants). The extractor device 100 described herein facilitates, tolerates, and transfers the high kinetic energy expended by the operator to the implant to disrupt the implant/bone interface and thereby affect the removal of the prosthetic component. In addition, the extractor device 100 is predicated on less invasive surgical techniques and exposure to minimize tissue and bone damage and optimize revision joint replacement procedures. As such, the present invention provides a more effective means to extract an implanted prosthetic component from the intramedullary canal. The overall goal achieved by the present invention is an efficient, less invasive, and facile means for extract an orthopaedic implant with a minimal amount of time, physical effort, and host tissue and bone damage.

In particular, the present disclosure provides a device 100 comprising (a) an elongated member 150 having a first end and a second end, the elongated member comprising substantially straight, rod-like first 120, second 140, and third 180 segments each having first and second ends, the first 120 and second 140 segments being connected by a first curved segment 130 at their second and first ends, respectively, and the second 140 and third 180 segments being connected by a second curved segment 160 at their second and first ends, respectively, and the first ends of each of the segments 120, 140 and 180 are proximal to the first end of the elongated member 150 relative to the second ends of the segments, (b) a first striking surface 110 positioned on the first segment 120 extending away from the elongated member 150, (c) a second striking surface 170 positioned on the third segment 180 extending away from the elongated member 150, and (d) a hook 190 positioned at the second end of the third segment 180, wherein the hook 190 includes a channel 210 substantially perpendicular to a long axis of the third segment 180 that is configured to engage a surgical implant.

Figure 7A:
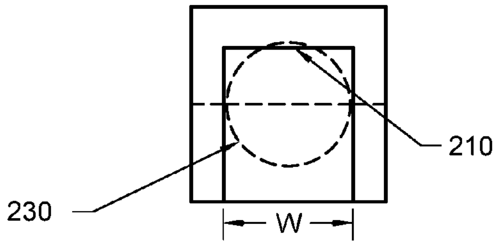
FIG. 7A illustrates a bottom view of a hook of the device of FIG. 1, according to an example embodiment.
Figure 7B:
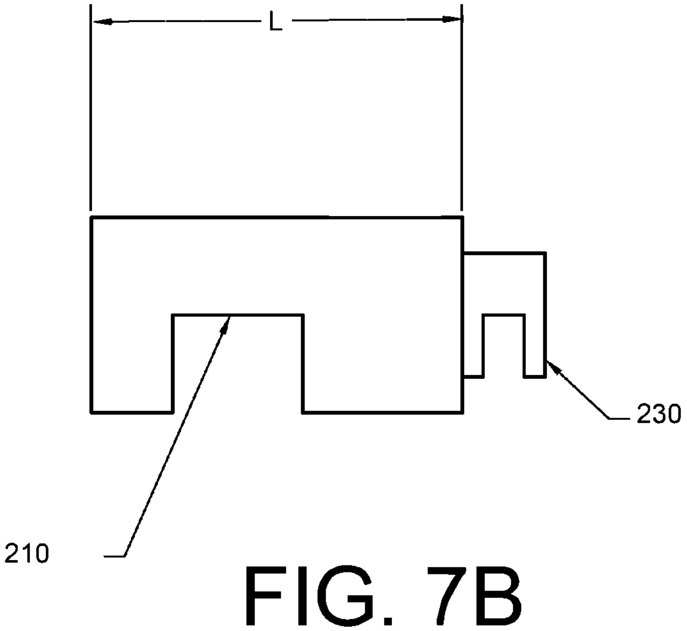
FIG. 7B illustrates a side view of the hook of FIG. 6A, according to an example embodiment.
Figure 8:
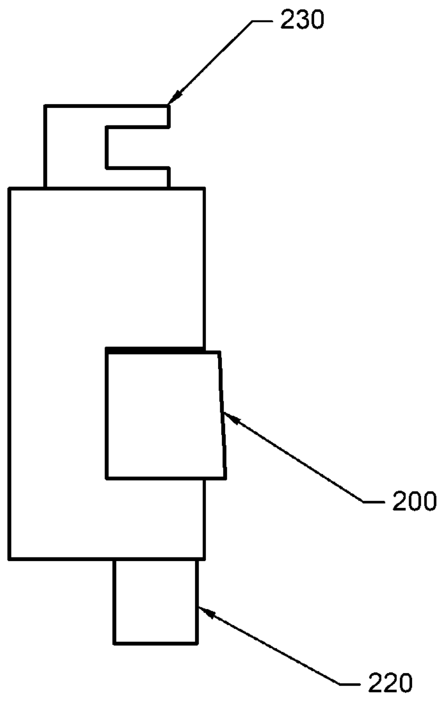
FIG. 8 illustrates a side view of the hook and lock of FIGS. 7A and 7B, according to an example embodiment.

The hook 190 and clamp mechanism may be integrated into the second end of the third segment or modular and variably sized such that it can be secured to the neck 220 of the implant distal to the implant neck 220 or trunnion 200. Each such hook 190 may be configured for attachment to a specific stein implant having a known shape, size and geometry. The hook 190 may have a length (L) ranging from about 2 cm to about 4 cm. The length (L) of the hook is measured from a centerline extending into the hook starting at the proximal end (the end adjacent to the elongated member) and continuing to the distal end. As such, the length (L) of the hook is measured in a direction parallel to the long axis of the third segment 180 of the elongated member 150, as shown in FIGS. 1 and 7B. The variable sizes are optimized to a specific prosthesis and configured to be smaller than the trunnion section of the implant but larger than the neck of the prosthesis to provide for a secure mechanical coupling and grip of the proximal implant. In another embodiment, the hook channel width (W) is adjustable for engaging a specific prosthesis. In one embodiment, the channel is U-shaped such that a side of the hook is open to receive the neck of the prosthesis. In some embodiments, the channel of the hook may have a width (W) ranging from about 2 cm to about 3 cm. The width (W) is measured from a first interior surface of the channel to a second interior surface of the channel in a direction perpendicular to the long axis of the third segment of the elongated member, as shown in FIGS. 1 and 7A.

In one example, the hook 190 is permanently affixed to the second end of the elongated member 150. In another example, the hook 190 is removably coupled to the second end of the elongated member 150. In such embodiments, the device may include a lock 230 between the second end of the elongated member 150 and the hook 190. Preferably the lock 230 connects the hook 190 to the second end of the elongated member 150 such that there is little or no play between the two components. In one particular example, the hook 190 may include a clip, and the second end of the elongated member 150 may include a lever configured to mate with the clip to thereby removably couple the hook to the elongated member. Other mechanisms for removably coupling the hook to the elongated member are possible as well.

Figure 3:
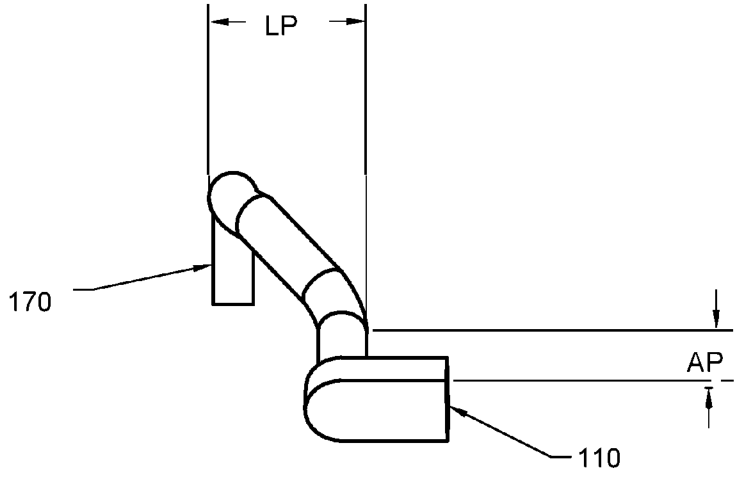
FIG. 3 illustrates a top view of the example device for a left hip of FIG. 1, according to an example embodiment.
Figure 9B:
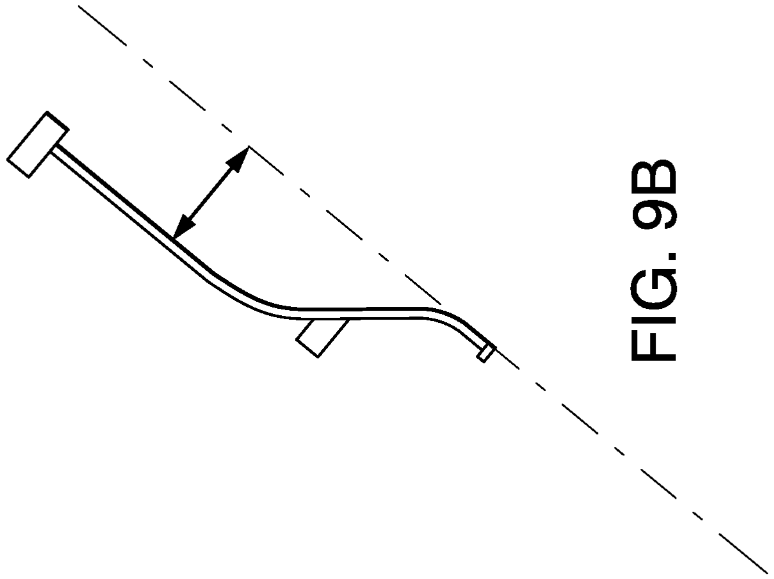
FIG. 9B illustrates a side view of another example device demonstrating the offset in the anterior plane, according to an example embodiment.
Figure 9A:
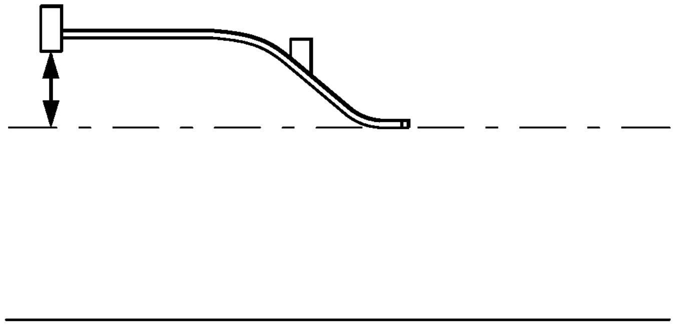
FIG. 9A illustrates a top view of another example device demonstrating the offset in the lateral plane, according to an example embodiment.
Figure 10:
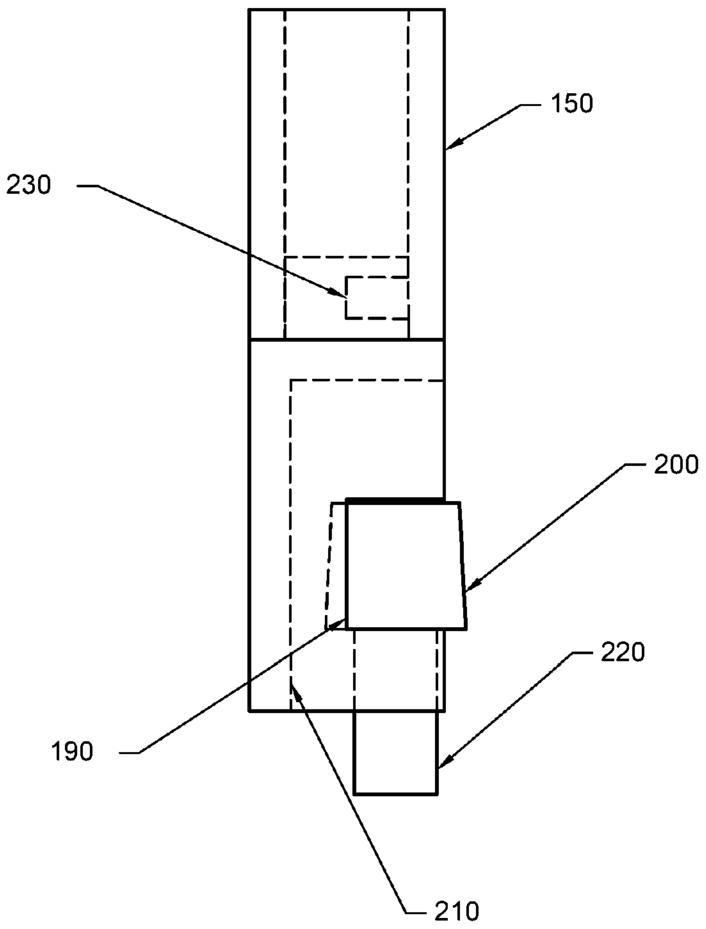
FIG. 10 illustrates a side view of the hook and lock, according to an example embodiment.
Figure 11:
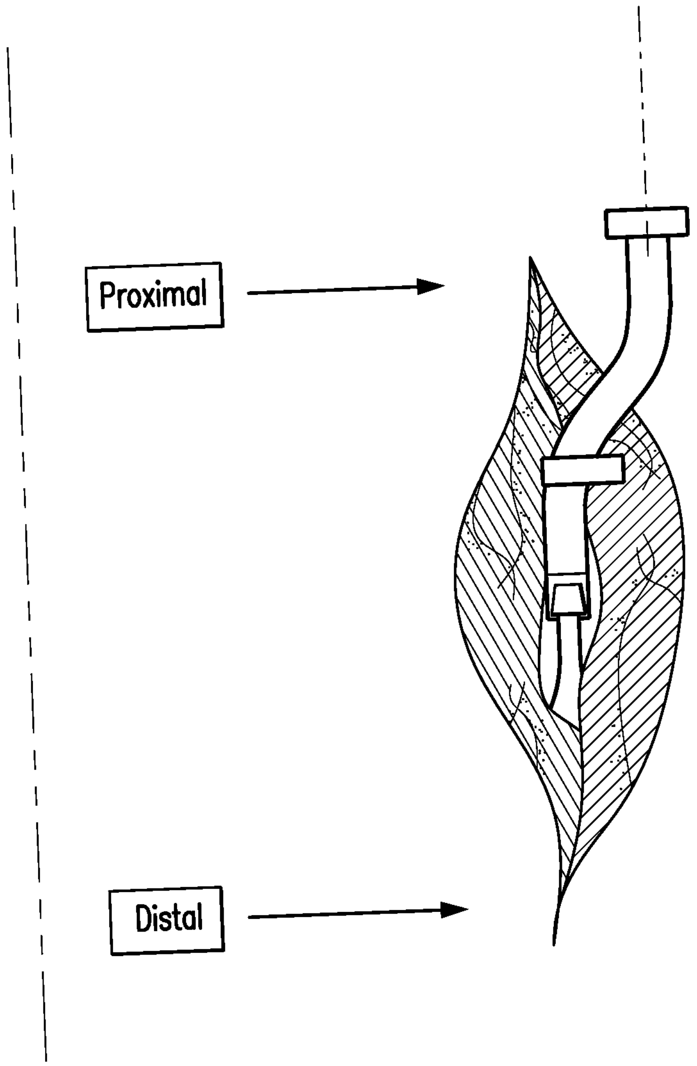
FIG. 11 illustrates a top view (left hip) of the elongated member engaged with the hook and lock as it secures onto the trunnion of the femoral component, according to an example embodiment.
Figure 12:
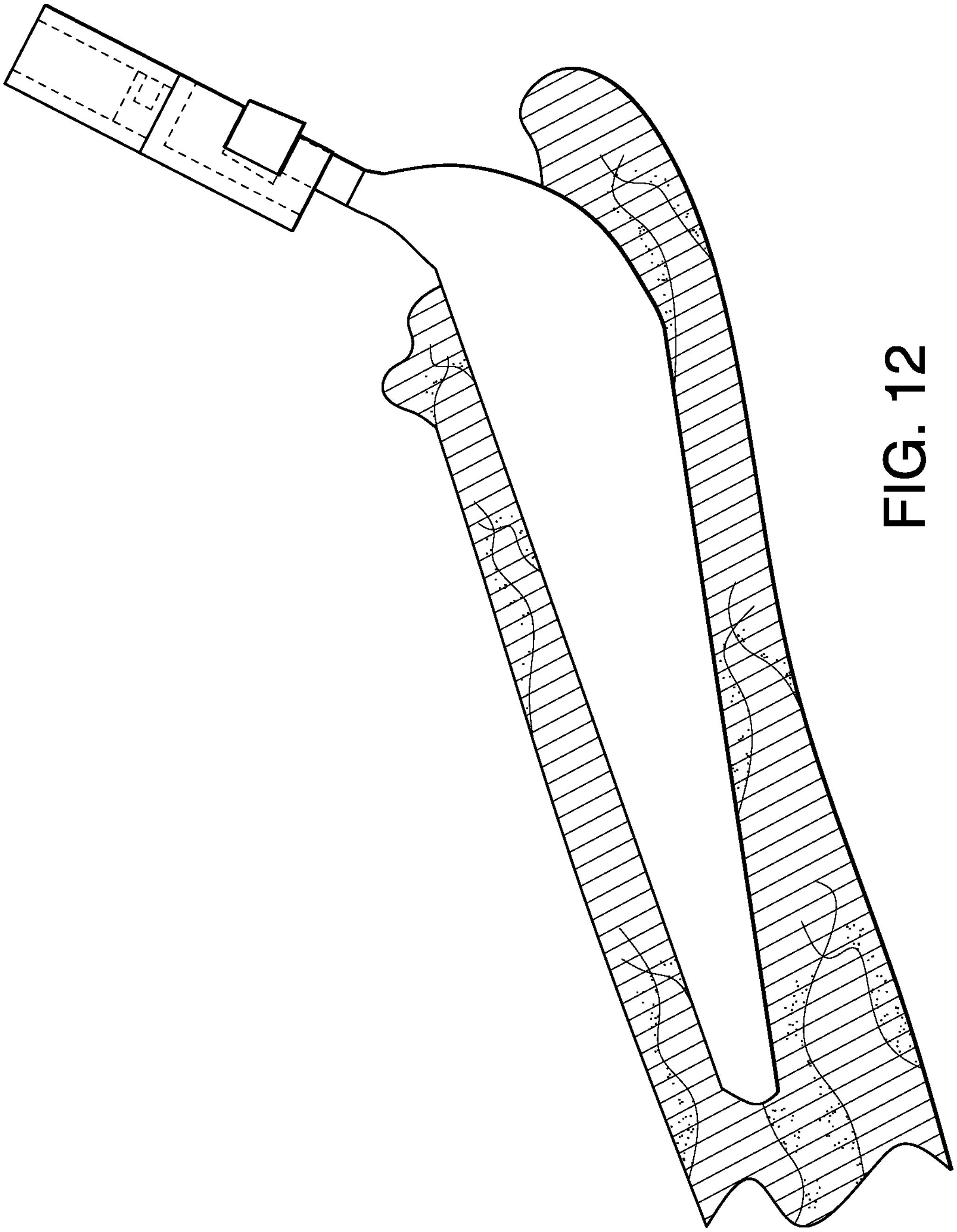
FIG. 12 illustrates a side view of the elongated member engaged with the hook and lock as it secures onto the trunnion of the femoral component, according to an example embodiment.
Figure 13:
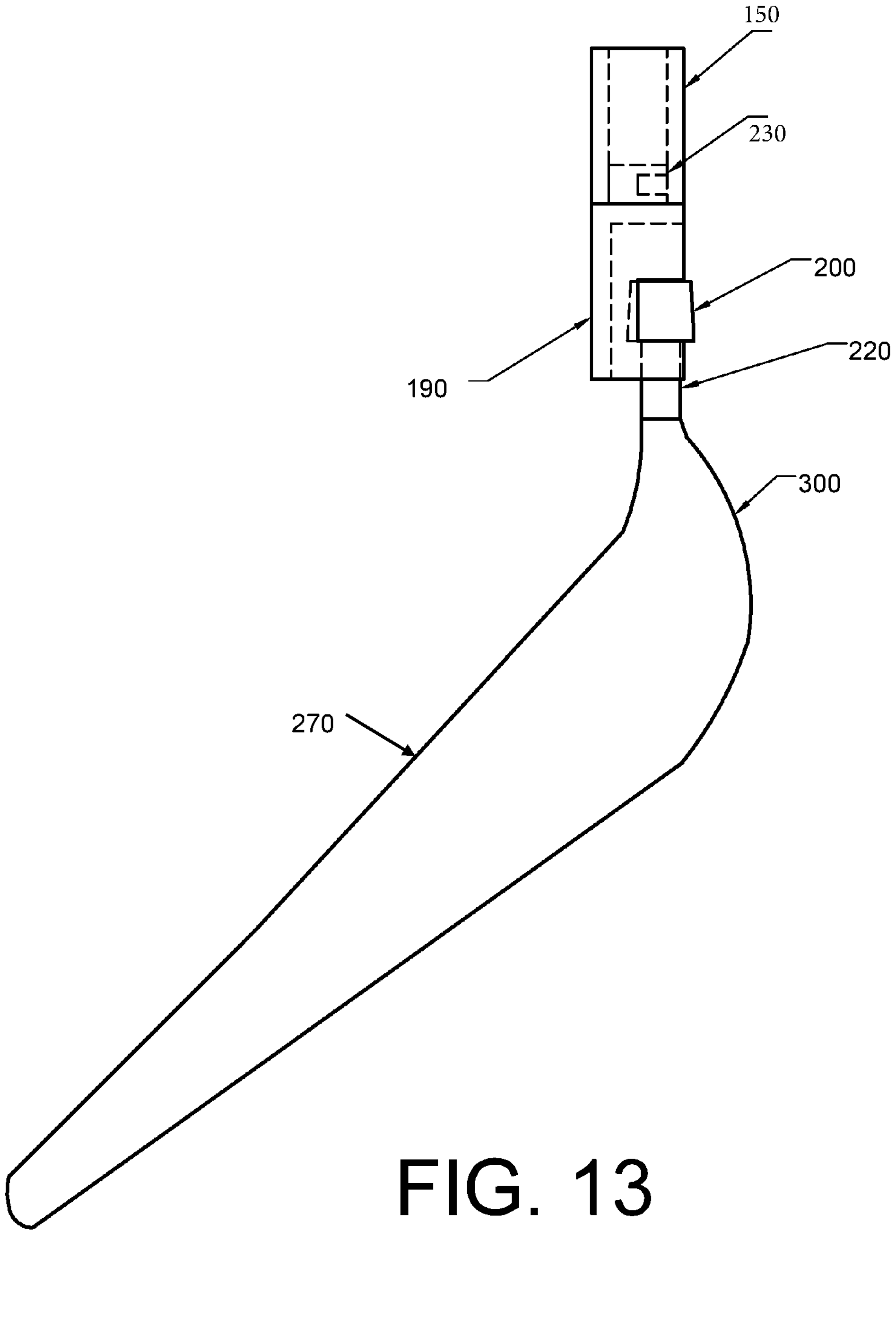
FIG. 13 illustrates a side view of the hook after engagement of the hook onto the trunnion, according to an example embodiment.

In one embodiment, the elongated member is offset in an anterior plane ("AP" in FIG. 3) with respect to the axis of a person's femur as shown in FIG. 9B and further offset in a lateral plane ("LP" in FIG. 3) with respect to the axis of a person's femur as shown in FIG. 9A. The lateral offset of the elongated member with respect to the axis of a patient's femur is further seen in FIG. 11. The anterior offset of the elongated member with respect to the axis of a person's femur is further seen in FIG. 12. As used herein, the "anterior plane" indicates a plane that is anterior to the ventral surface of the patient, e.g. ventral to the coronal midaxis of the patient's body. As used herein, the "lateral plane" indicates a plane lateral to the sagittal plane of the patient, e.g. lateral to the sagittal midaxis of the patient's body. The anterior offset and lateral offset are in essence in perpendicular planes to each other.

The elongated member transitions at an optimal angle to permit both the transmission of force to the implant and for its use in less invasive surgical procedures. In particular, the elongated member is offset in the anterior plane between about 30 degrees and about 50 degrees, and the elongated member is offset in the lateral plane between about 40 degrees and about 60 degrees. Offset in the anterior plane refers to an angled deviation from the mid-ventral surface of the patient in the coronal plane and offset in the lateral plane refers to an angled deviation from the midline axis of the patient in the sagittal plane, as illustrated in FIGS. 1-4.

In one example, as shown in FIG. 1, the elongated member 150 comprises a first segment 120, a second segment 140, and a third segment 180. The first segment 120 is positioned at the first end of the elongated member 150, the third segment 180 is positioned at the second end of the elongated member 150, and the second segment 140 is positioned between the first segment 120 and the third segment 180. In such an example, the first, second, and third segments are substantially straight and rod-like. The first segment has a length ranging from about 10 cm to about 15 cm, the second segment has a length ranging from about 12 cm to about 17 cm, and the third segment has a length ranging from about 12 cm to about 18 cm. In one example, each of the first, second, and third segments have different lengths. In another example, each of the first, second, and third segments have the same lengths. In another example, the first and second segments have the same length, while the third segment has a different length. In another example, the first and third segments have the same length, while the second segment has a different length. In yet another example, the second and third segments have the same length, while the first segment has a different length.

The cross-sections of the segments 120, 140, 180 can be any convenient shape, such as round, elliptical, square, or rectangular, but typically they will be round. The first segment has a diameter ranging from about 2 cm to about 4 cm, the second segment has a diameter ranging from about 2 cm to about 4 cm, and the third segment has a diameter ranging from about 2 cm to about 4 cm. In one example, each of the first, second, and third segments have different diameters. In another example, each of the first, second, and third segments have the same diameters. In another example, the first and second segments have the same diameter, while the third segment has a different diameter. In another example, the first and third segments have the same diameter, while the second segment has a different diameter. In yet another example, the second and third segments have the same diameter, while the first segment has a different diameter. When the cross-sections are shaped differently than a circle their general size will be the same as described above.

As shown in FIG. 1, the first 120 and second 140 segments are connected by a first curved segment 130 at their second and first ends, respectively, and the second 140 and third 180 segments being connected by a second curved segment 160 at their second and first ends, respectively. As used herein, "curved" means a segment that is bent at an angle or, more frequently, has a continuously bending centerline. The first 130 and second 160 curved sections provide an offset in an anterior plane and a further offset in a lateral plane. In particular, as shown in FIG. 4, the long axes of the second and third segments are located in a first plane. The angle between the long axis of the third segment and the long axis of the second segment (labeled angle 1 in FIG. 5B) may range from between about 40 degrees and about 60 degrees, which represents an offset in the lateral plane. The first and second segments are located in a second plane that is different than the first plane. The first segment has an angle ranging between about 30 degrees and about 50 degrees with respect to the long axis of the third segment (labeled angle 2 in FIG. 5C) and an angle ranging between about 40 degrees and about 100 degrees with respect to an axis in the first plane that is perpendicular to the long axis of the third segment.

In one particular example, the second segment 140 curves in a direction away from the anterior plane and a direction away from the lateral plane. In one example, the first striking surface 110 extends away from the first segment 120 of the elongated member 150 in a direction substantially perpendicular to the long axis of the first segment 120 and away from the midline axis "M" of the patient as shown in FIG. 1, and the second striking surface 170 extends away from the third segment 180 of the elongated member 150 in a direction substantially perpendicular to the long axis of the third segment 180 and away from the channel 210 in the lock 230. In another example, the first striking surface 110 extends away from the first segment 120 of the elongated member 150 in a direction substantially perpendicular to the long axis of the first segment 120 and away from the midline axis "M" of the patient as shown in FIG. 1, and the second striking surface 170 extends away from the second segment 140 of the elongated member 150 in a direction substantially perpendicular to the long axis of the third segment 180 and away from the channel 210 in the lock 230. Other arrangements are possible as well.

In one example, the device may comprise a kit including two elongated members, one left and one right. Only one elongated member is coupled to the lock at a given time. The left and right elongated members may be mirror images of one another. The left elongated member would be used to extract a femoral implant positioned in the left hip of a patient, while the right elongated member would be used to extract a femoral implant positioned in the right hip of the patient. In one example, the kit does not include the lock. In another example, the kit includes a single lock. Only one elongated member is coupled to the lock at a given time. The lock may be decoupled from the right elongated member and coupled to the left elongated member when a medical professional extracts a femoral implant positioned in the left hip of a patient. In another example, each of the left and right elongated members includes its own lock as part of the kit.

As discussed above, the elongated member 150 may further include two striking surfaces 110, 170 extending away from the elongated member. In one example, the length of the first striking surface 110 is equal to the length of the second striking surface 170. The length of the first striking surface is measured from a first end to a second end of the first striking surface along a long axis of the first striking surface, and the length of the second striking surface is as measured from a first end to a second end of the second striking surface along a long axis of the second striking surface. In another example, the length of the second striking surface is greater than the length of the second striking surface. The elongated member 150 may have a length ranging from about 15 cm to about 25 cm. As used herein, the length of the elongated member comprises the arc length, or the length of the centerline of the elongated member, from the first end to the second end. The first striking surface 110 may have a length ranging from about 3 cm to about 5 cm, and the second striking surface 170 may have a length ranging from about 15 cm to about 17 cm.

Generally, the first 110 and second 170 striking surfaces comprise a protrusion capable of transferring the force from the impact of a hammer strike to the elongated member 150. More particularly, the first and second striking surfaces comprise a protrusion from the elongated member, preferably principally in a direction perpendicular to a longitudinal line or tangent to a generally longitudinal arc along the length of the hook 190 at the location of the protrusion. In particular, the first striking surface 110 extends away from a long axis of the first segment 120 in a substantially perpendicular direction to the long axis of the first segment 120 at the point at which the first striking surface 110 is positioned, and the second striking surface 170 extends away from a long axis of the third segment 180 in a substantially perpendicular direction to the long axis of the third segment 180 at the point at which the second striking surface 170 is positioned. As such, the long axes of the first and second striking surfaces may be substantially parallel to one another. The first and second striking surfaces can be rounded or comprise a flat surface for receiving hammer strikes. The longitudinal direction of the first and second striking surfaces extends in a direction away from the anterior plane.

The first 110 and second 170 striking surfaces on the elongated member 150 are designed to tolerate and transfer the impact of a strike (e.g., a hammer strike) by the operator and transmit the force to disrupt the prosthetic/bone interface. In one example, the first striking surface may be positioned between the first end of the elongated member and the second striking surface. In another example, the first striking surface may be positioned at the first end of the elongated member. The first striking surface is generally positioned near the first end of the elongated member (e.g., within 5 cm of the first end of the elongated member). The second striking surface may be positioned at the first end of the third segment of the elongated member. As shown in FIG. 1, the second striking surface may be positioned near the second curved segment 160 of the elongated member. The materials that make up the device, including the elongated member 150, the first 110 and second 170 striking surfaces, and the hook 190, would be corrosion resistant electropolished stainless steel typical of orthopedic devices, or other metal alloys that allow for sterilization without mechanical deformation.

The foregoing describes an implant extractor device 100 to facilitate the removal of a femoral component 270 of a hip joint prosthesis, as one particular non-limiting example. Femoral implants 270 have a trunnion 200, neck 220, and shoulder 300 region which are proximal to the stein that is implanted into the proximal medullar cavity of the femur 310. The device described herein may be secured to the stein at the junction of the trunnion 200 and the neck 220 of the implant. The hook and clamp contains a channel of sufficient size to receive the neck of the implant, but small enough to deny passage of the trunnion through it. As such, the hook takes advantage of the differential between the size of the trunnion and the size of the neck of the implant. The clamp mechanism can accept a range of trunnion sizes. Due to the varying sizes of implant necks, multiple sizes of the hooks and excursion of the clamp would be necessary, hence the modularity and/or adjustability of the clamp. In addition, the hook is secured to the elongated member, which is offset in two planes, anteriorly and laterally, permitting the application of the device in an easy, secure, and less invasive manner. The force generated by the operator will then be transmitted efficiently to the implant via the device so as to effect the prosthetic removal.

In another exemplary embodiment as shown in FIGS. 14 through 19, the present disclosure provides a device 500 comprising an elongated member with three general sections. The three sections each make up essential components of an exemplary orthopaedic extractor device 500.

The first section 510 contains a clamp mechanism 600 that attaches to the orthopaedic implant. The clamping mechanism 600 includes a channel 610 substantially perpendicular to the long axis that is configured to engage the orthopaedic implant and secure it for removal. The clamping mechanism is shown in further detail in FIGS. 17-19.

This first section 510 is a substantially straight, rod-like segment which connects to the second section 520. The second section 520 is a curved segment and contains a first 540 of two striking plates which is positioned to extend away from the elongated member. The third section 530 is a substantially straight, rod-like segment that contains the second 550 of two striking plates that extend away from the elongated member.

The clamping mechanism 600 is integrated into the first segment 510 and permits variably sized orthopaedic implants to be placed into the channel 610 to be secured to enable extraction of the implant from the intramedullary cavity. The axis through which the clamping mechanism directs force onto the implant is directed at a 45 degree angle from the perpendicular axis of the face of the proximal aspect of the first section 510. Once the femoral component is introduced into the channel 610 of the first section of the extractor, the clamp 600 can then be tightened and thereby attached to the section of the implant distal to the implant neck (also known as the femoral trunnion). The clamping mechanism 600 may be variably tightened for securing the attachment to orthopaedic implants having variable shapes, sizes and geometries. The clamping mechanism 600 is shown in an open position in FIG. 18, and in a closed position in FIG. 19. The clamp mechanism may have a length ranging from about 2 cm to about 3 cm. The length of the locking mechanism 640 is measured from a centerline extending into the locking mechanism starting at the proximal end (the end adjacent to the elongated member) and continuing to the distal end. As such, the length of the locking mechanism 640 is measured in a direction parallel to the long axis of the first segment 610 of the elongated member. The variability of the clamp compression is afforded through a locking bolt 630 and swivel 650 of the locking mechanism 640 that can be tightened and thereby opened and closed to apply compression to a range of prosthesis dimensions. The bolt activated compression is produced by extension on the distal end of the clamp mechanism across a fulcrum 620 that produces compression on the proximal aspect of the clamp 640. The proximal aspect of the clamp can be tightened around the neck of the implant which is generally of a smaller diameter than the trunnion section of the implant to provide for a secure mechanical coupling and grip of the proximal implant.

In another embodiment, the width of the clamping mechanism channel 610 is adjustable for engaging a range of prostheses. In one embodiment, the channel is U-shaped such that a side of the locking mechanism is open to receive the neck of the prosthesis. In some embodiments, the channel of the locking mechanism may have a width ranging from about 0.75 cm to about 1 cm. The width is measured from a first interior surface of the channel to a second interior surface of the channel in a direction perpendicular to the long axis of the first segment of the elongated member. In one example, the locking mechanism is permanently affixed to the second end of the elongated member.

In one embodiment, second section 520 of the elongated member affords offset in two planes: anterior plane offset 570 and further secondary offset in the lateral plane 560. As used herein, the "anterior plane" indicates a plane that is anterior to the ventral surface of the patient, e.g. ventral to the coronal midaxis of the patient's body. As used herein, the "lateral plane" indicates a plane lateral to the sagittal plane of the patient, e.g. lateral to the sagittal midaxis of the patient's body. The anterior offset and lateral offset are in essence in perpendicular planes to each other.

The elongated member transitions at an optimal angle to permit both the transmission of force to the implant and for its application in less invasive orthopaedic surgical procedures. In particular, offset of the orthopaedic femoral extractor is afforded through the second section of the elongated member. Offset is created in two planes: in the anterior plane between about 30 degrees and about 50 degrees, and the lateral plane between about 40 degrees and 60 degrees. Offset in the anterior plane refers to an angled deviation from the mid-ventral surface of the patient in the coronal plane and offset in the lateral plane refers to an angled deviation from the midline axis of the patient in the sagittal plane.

Figure 14:
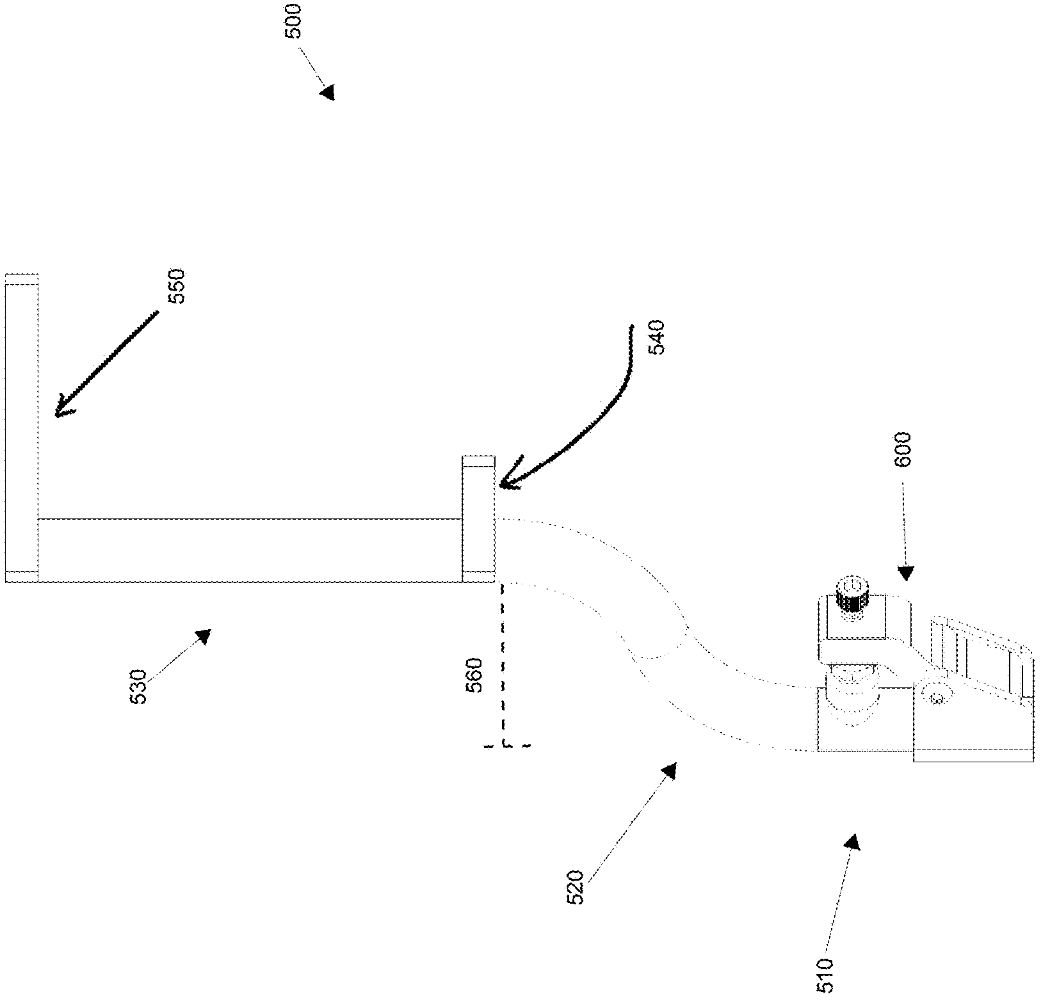
FIG. 14 illustrates a top view of an example device, with the associated clamp mechanism according to an example embodiment.
Figure 15:
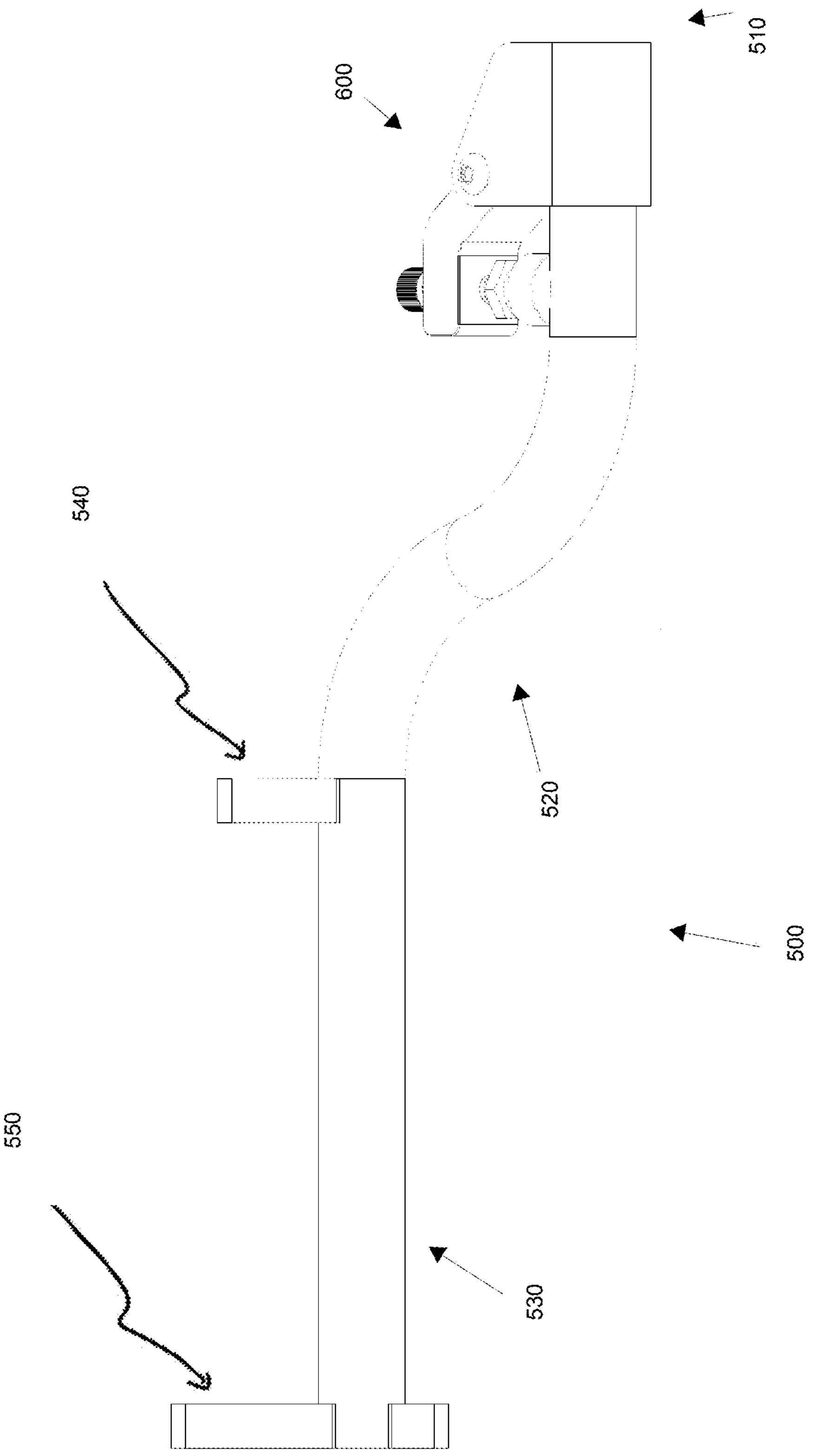
FIG. 15 illustrates a side view of an example device, with the associated clamp mechanism according to an example embodiment.
Figure 16:
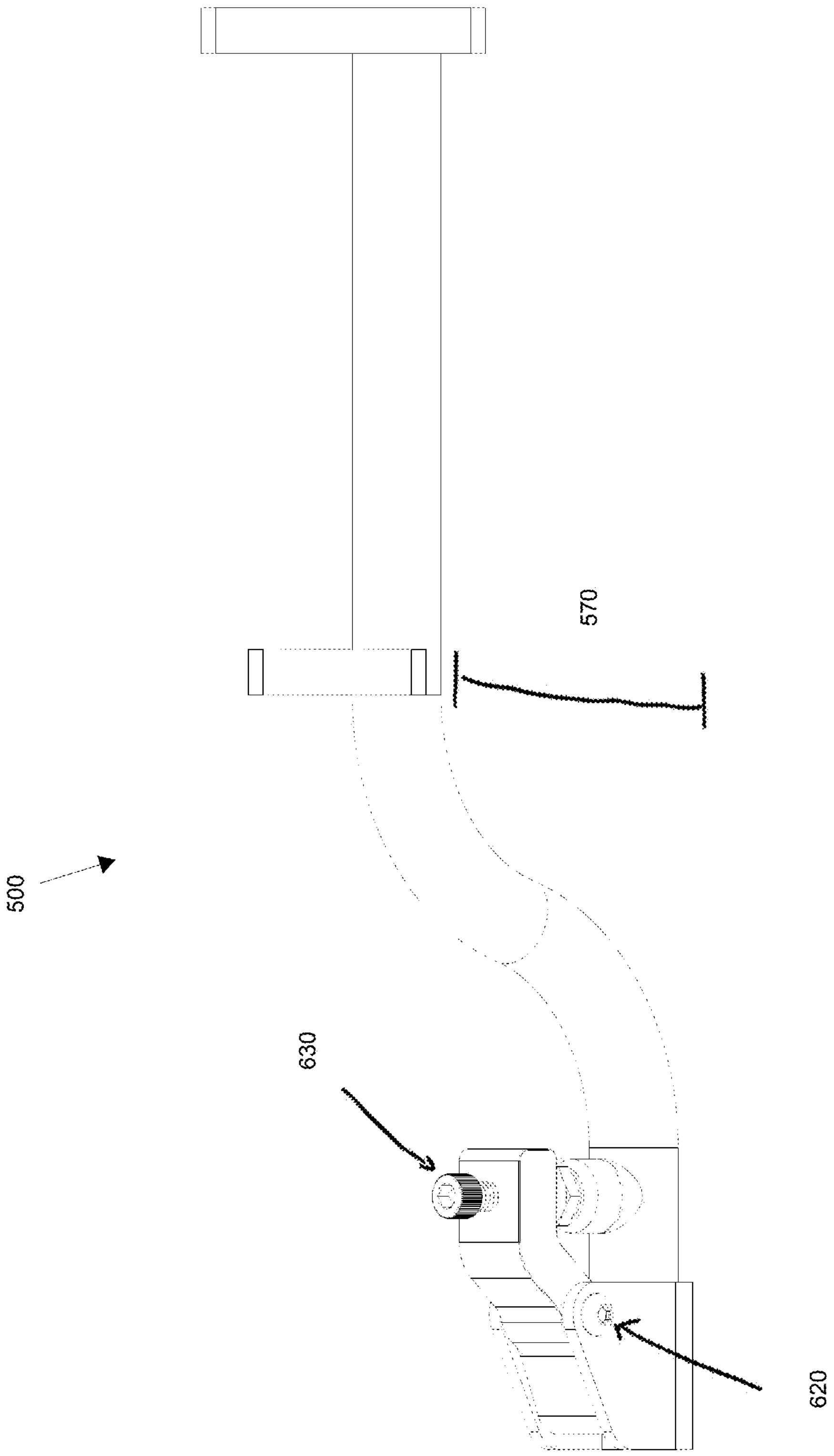
FIG. 16 illustrates a top view of an example device, with the associated clamp mechanism according to an example embodiment.
Figure 17:
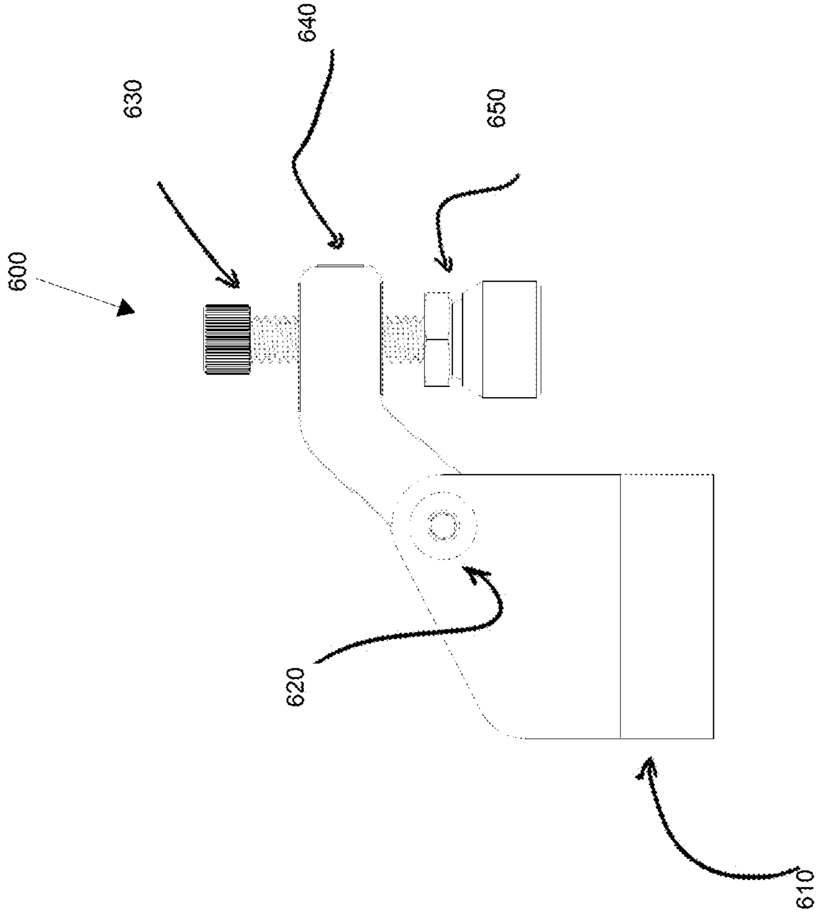
FIG. 17 illustrates a side view of the clamping mechanism, and associated channel for the trunnion of the femoral component according to an example embodiment.
Figure 18:
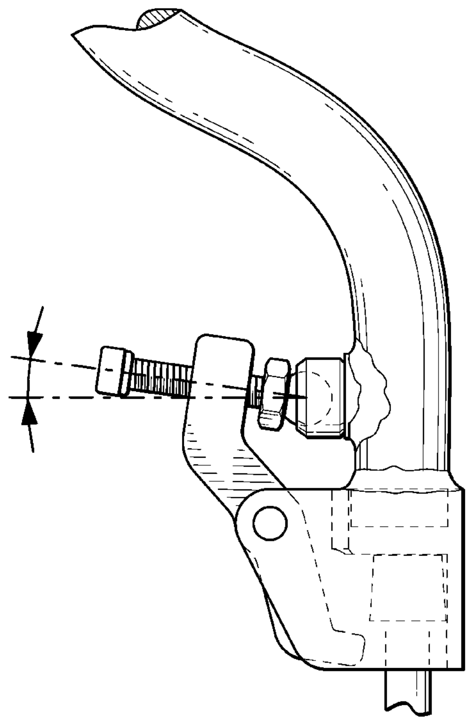
FIG. 18 illustrates a side view of the clamping mechanism with the clamp mechanism in an open position to accept the introduction of the trunnion, according to an example embodiment.
Figure 19:
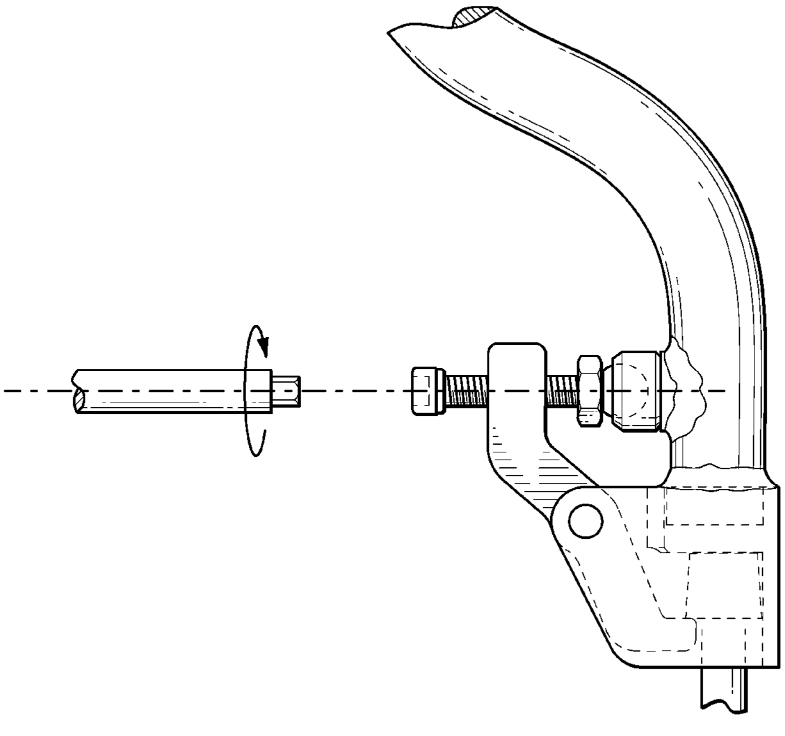
FIG. 19 illustrates a side view of the clamping mechanism with the clamp mechanism in a closed position, securing the trunnion of the femoral component, according to an example embodiment.

In one example, as shown in FIGS. 14 through 16, the femoral extractor device comprises a first, second, and third segments. The first segment, comprising the clamping mechanism, has a length ranging from about 2 cm to 4 cm, the second segment has a length ranging from about 12 cm to about 15 cm, and the third segment has a length ranging from about 14 cm to about 16 cm. In one example, each of the first, second, and third segments have different lengths. The cross-sections of the segments can be any convenient shape, such as round, square, or rectangular, but typically they will be uniform, rounded, and rectangular in dimension. The three segments have a diameter ranging from about 2 cm to about 4 cm.

As shown in FIGS. 14 through 16, the first and third segments are connected by the second segment which is a substantially curved segment affording anterior and lateral offset. As used herein, "curved" means a segment that is bent at an angle or, more frequently, has a continuously bending centerline. In particular, the long axes of the first and third segments are located in a parallel plane. The angle between the long axis of the first segment and the long axis of the third segment may range from between about 40 degrees and about 60 degrees, which represents offset in the lateral plane. The first segment has an angle ranging between about 30 degrees and about 50 degrees with respect to the long axis of the third segment and an angle ranging between about 40 degrees and about 60 degrees with respect to an axis in the first plane that is perpendicular to the long axis of the third segment.

In another example, the second segment curves in a direction away from the anterior plane and a direction away from the lateral plane. In one example, the first striking surface extends away from the second segment of the elongated member in a direction substantially perpendicular to the long axis of the second segment and away from the midline axis of the patient, and the second striking surface extends away from the third segment of the elongated member in a direction substantially perpendicular to the long axis of the third segment. In another example, the first striking surface extends away from the second segment of the elongated member in a direction substantially perpendicular to the long axis of the second segment and away from the midline axis of the patient, and the second striking surface extends away from the third segment of the elongated member in a direction substantially perpendicular to the long axis of the third segment and away from the channel in the clamping mechanism.

In one example, the device may comprise a kit including two elongated members, one left and one right. The left and right elongated members may be mirror images of one another. The left elongated member would be used to extract a femoral implant positioned in the left hip of a patient, while the right elongated member would be used to extract a femoral implant positioned in the right hip of the patient.

As discussed above, the elongated member may further include two striking surfaces extending away from the elongated member. In one example, the length of the first striking surface is smaller than the length of the second striking surface. The length of the first striking surface is measured from a first end to a second end of the first striking surface along a long axis of the first striking surface, and the length of the second striking surface is as measured from a first end to a second end of the second striking surface along a long axis of the second striking surface. The elongated member may have a total length ranging from about 28 cm to about 35 cm. As used herein, the length of the elongated member comprises the arc length, or the length of the centerline of the elongated member, from the first end to the second end. The first striking surface may have a length ranging from about 5 cm to about 7 cm, and the second striking surface may have a length ranging from about 9 cm to about 12 cm.

Generally, the first and second striking surfaces comprise a protrusion capable of transferring the force from the impact of a hammer strike to the elongated member. More particularly, the first and second striking surfaces comprise a protrusion from the elongated member, preferably principally in a direction perpendicular to a longitudinal line or tangent to a generally longitudinal arc along the length of the clamping mechanism at the location of the protrusion. In particular, the first striking surface extends away from a long axis of the first segment in a substantially perpendicular direction to the long axis of the first segment at the point at which the first striking surface is positioned, and the second striking surface extends away from a long axis of the third segment in a substantially perpendicular direction to the long axis of the third segment at the point at which the second striking surface is positioned. As such, the long axes of the first and second striking surfaces may be substantially parallel to one another. The first and second striking surfaces can be rounded or comprise a flat surface for receiving hammer strikes. The longitudinal direction of the first and second striking surfaces extends in a direction away from the anterior plane.

The first and second striking surfaces on the elongated member are designed to tolerate and transfer the impact of a strike (e.g., a hammer strike) by the operator and transmit the force to disrupt the prosthetic/bone or prosthetic/cement interface. In one example, the first striking surface may be positioned at the junction of the second and third segments. The second striking surface may be positioned at the distal aspect of the third segment. As shown in FIG. 1, the first striking surface may be positioned at the distal aspect of the second segment (the curved segment) of the elongated member. The materials that make up the device, including the elongated member, the first and second striking surfaces, and the locking mechanism, would be corrosion resistant stainless steel typical of orthopedic devices, or other metal alloys that allow for sterilization without significant deformation.

The foregoing describes an orthopaedic implant extractor device to facilitate the removal of a femoral component of a hip joint prosthesis, as one particular non-limiting example. Femoral implants have a trunnion, neck, and shoulder region which are the proximal embodiment of the stein that is implanted into the proximal intramedullary cavity of the femur during a hip arthroplasty procedure. The device described herein may be tightly secured to the stein at the junction of the trunnion and the neck of the implant. The clamping mechanism contains a channel of sufficient size to receive the neck and trunnion of the implant, and once the clamp is applied, it is then small enough to deny passage of the trunnion through it. As such, the clamping mechanism takes advantage of the differential between the size of the trunnion and the size of the neck of the implant. In addition, the locking mechanism is secured to the elongated member, which is offset in two planes, anteriorly and laterally, permitting the application of the device in an easy, secure, and less invasive manner. The force generated by the operator will then be transmitted efficiently to the implant via the device so as to effect the prosthetic implant removal.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

I claim:

1. A device comprising:

an elongated member having a first end and a second end, the elongated member comprising substantially straight, rod-like first and third segments each having first and second ends, the first and third segments being connected by a substantially curved second segment at their second and first ends, respectively, wherein the second segment offsets the elongated member in an anterior plane and a lateral plane;

a first striking surface positioned on the second segment extending away from the elongated member;

a second striking surface positioned on the third segment extending away from the elongated member; and a clamping mechanism positioned on the first segment, wherein the clamping mechanism is defined by a channel that extends in a direction substantially perpendicular to a long axis of the first segment that is configured to engage a proximal portion of a surgical prosthetic implant.

2. The device of claim 1, wherein a length of the first striking surface as measured from a first end to a second end of the first striking surface along a long axis of the first striking surface is smaller than the length of the second striking surface as measured from a first end to a second end of the second striking surface along a long axis of the second striking surface.

3. The device of claim 1, wherein a length of the second striking surface as measured from a first end to a second end of the second striking surface along a long axis of the second striking surface is greater than a length of the first striking surface as measured from a first end to a second end of the first striking surface along a long axis of the first striking surface.

4. The device of claim 1, wherein the elongated member is offset in an anterior plane and further offset in a lateral plane.

5. The device of claim 1, wherein an angle between a long axis of the first segment and the long axis of the third segment ranges from about 30 degrees to about 50 degrees, and wherein an angle between the perpendicular plane to the long axis of the first and third segments ranges from about 40 degrees to about 60 degrees.

6. The device of claim 1, wherein a long axis of the elongated member extending through the center of the elongated member from the first end to the second end has a length ranging from about 20 cm to about 30 cm.

7. The device of claim 1, wherein the channel for the introduction of the prosthetic implant has a width in a direction perpendicular to the long axis of the first segment ranging from about 0.6 cm to about 0.75 cm.

8. The device of claim 1, wherein the clamping mechanism has a length in a direction parallel to the long axis of the first segment ranging from about 2 cm to about 4 cm.

9. The device of claim 1, wherein the first striking surface has a length ranging from about 1 cm to about 2 cm as measured from a first end to a second end of the first striking surface along a long axis of the first striking surface, and wherein the second striking surface has a length ranging from about 7 cm to about 9 cm as measured from a first end to a second end of the second striking surface along a long axis of the second striking surface.

10. The device of claim 1, wherein the clamping mechanism comprises a swivel bolt.

11. The device of claim 10, wherein tightening of the swivel bolt changes a width of the channel.

12. The device of claim 1, wherein the elongated member comprises stainless steel or metal alloys suitable for sterilization and autoclaving without deformity.

13. The device of claim 1, wherein the first striking surface is positioned at the junction of the second and third segments.

14. The device of claim 1, wherein the second striking surface is positioned at the distal end of the third segment of the elongated member.

15. The device of claim 1, wherein the first striking surface extends away from a long axis of the second segment in a substantially perpendicular direction to the long axis of the second segment at the point at which the first striking surface is positioned, and wherein the second striking surface extends away from a long axis of the third segment in a substantially perpendicular direction to the long axis of the third segment at the point at which the second striking surface is positioned.

* * * * *